United States Patent [19]

Powell, III et al.

[11] Patent Number: 5,358,513
[45] Date of Patent: Oct. 25, 1994

[54] PARAMETER SELECTION AND ELECTRODE PLACEMENT OF NEUROMUSCULAR ELECTRICAL STIMULATION APPARATUS

[75] Inventors: Jack H. Powell, III; Joseph J. Seaman, both of Newman; Russell A. Foley, Fayetteville; JoAnn Leahy, Atlanta, all of Ga.

[73] Assignee: Medtronic, Inc., Minneapolis, Minn.

[21] Appl. No.: 987,851

[22] Filed: Dec. 9, 1992

[51] Int. Cl.⁵ .............................................. A61N 1/36
[52] U.S. Cl. ........................................ 607/48; 607/46
[58] Field of Search ................... 607/2, 46, 48, 49, 72, 607/74

[56] References Cited

U.S. PATENT DOCUMENTS 3,083,712  4/1963  Keegan, Jr. ........................... 607/48
5,097,833  3/1992  Campos ................................ 607/46

OTHER PUBLICATIONS

"Prevention of Venous Thromboembolism" by M. D. Stringer and V. V. Kakkar, Herz 14(1989), pp. 135–147, (Nr. 3).

"A Simple Way to Combat the Venous Stasis Which Occurs in the Lower Limbs During Surgical Operations" by F. S. A. Doran et al., British Journal of Surgery, 1964, vol. 51, No. 7, Jul., pp. 486–492.

"Optimal Electrical Stimulus for Prevention of Deep Vein Thrombosis" by A. N. Nicolaides et al., British Medical Journal, Sep. 23, 1972, pp. 756–758.

"Electrically Induced Short-Lasting Tetanus of the Calf Muscles for Prevention of Deep Vein Thrombosis" by Bjorn Lindstrom et al., British Journal of Surgery, vol. 69 (1982) 203–206.

"Effect of Intermittent Compression of the Arms on Deep Venous Thrombosis in the Legs" by M. T. N. Knight et al., The Lancet, Dec. 11, 1976, pp. 1265–1268.

"Functional Electric Stimulation to Enhance Systemic Fibrinolytic Activity in Spinal Cord Injury Patients" by Richard T. Katz et al., Arch Phys Med Rehabil, vol. 68, Jul. 1987, pp. 423–426.

"Deep Vein Thrombosis: Prophylaxis in Acute Spinal Cord Injured Patients" by Geno J. Merli et al., Arch Phys Med Rehabil, vol. 69, Sep. 1988, pp., 661–664.

"Intermittent Sequential Pneumatic Compression of the Legs and Thromboembolism-Deterrent Stockings in the Prevention of Postoperative Deep Venous Thrombosis" by A. N. Nicolaides et al., Surgery, Jul. 1983, pp. 21–25.

Primary Examiner—William E. Kamm
Assistant Examiner—Scott M. Getzow
Attorney, Agent, or Firm—Daniel W. Latham; Harold R. Patton

[57] ABSTRACT

A method of neuro-muscular electrical stimulation for treatment and prevention of venous thrombosis and pulmonary embolism employs electrodes attached to an anterior portion of a patient's knee, immediately proximal the common peroneal nerve. Electrical stimulation is comprised of trains of pulse modulated sinusoids where each pulse has a rise time of about 1 second, a fall time of about 0.5 seconds, and a plateau (on time) of about 1 to 10 seconds. Peroneal nerve stimulation is achieved thereby causing passive stretching of the gastrocnemius and soleus muscles (major posterior calf muscles) rather than a contraction for creating a blood pumping action.

12 Claims, 2 Drawing Sheets

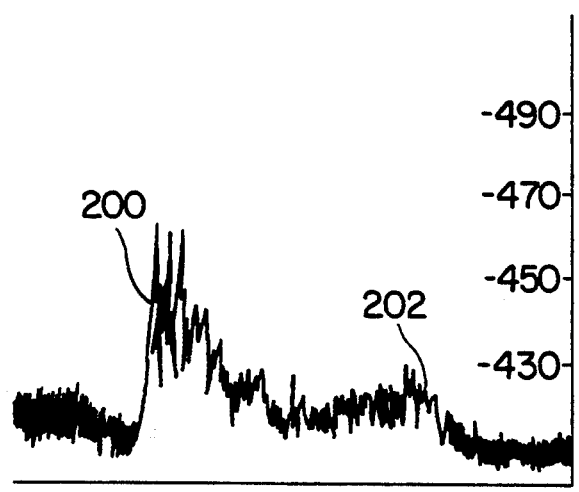
F I G. 5

PARAMETER SELECTION AND ELECTRODE PLACEMENT OF NEUROMUSCULAR ELECTRICAL STIMULATION APPARATUS

FIELD OF THE INVENTION

This invention relates generally to use of neuro-muscular electrical stimulation of the lower extremity for treatment and prevention of thrombosis, and more particularly to electrical stimulation of anterior to anterior lateral compartments exclusively of a patient's leg to promote venous blood flow.

BACKGROUND OF THE INVENTION

Prevention of venous thrombosis and pulmonary embolism is one of the major concerns of clinicians nationally. Pulmonary embolism is estimated to be the third most common cause of death in the United States. Hospitalization due to venous thrombosis and pulmonary embolism are associated in ranges of 300,000 to 600,000 a year and results in as many as 50,000 to 200,000 deaths a year as a result of pulmonary embolism.

Patients undergoing various types of surgical procedures as well as trauma are at high risk for developing deep vein thrombosis (DVT) and pulmonary embolism (PE). Averages demonstrate that the orthopedic patient population appear to be especially prone to thrombosis with highest risk in those patients with hip, tibial and knee fractures.

Factors contributing to the development of deep vein thrombosis include vascular stasis, coagulation changes, and blood vessel damage. It is generally believed that slowing of the blood flow or blood return system from the legs during and after surgery, is the primary factor related to the development of DVT. It appears that this slowing has its greatest effect during the intraoperative phase, but is also of concern during the postoperative period.

Recent evidence, documented by Kakkar, V. V.: Prevention of venous thrombo embolism., Clin. Haemat. 10 (1981), 543–582, has identified a possible "fibrinolysis shutdown" contribution to clot formation. These factors are notably combined in orthopedic operations on the lower-limb which are recognized high risk procedures.

The body's normal physiologic mechanism to return fluid to the heart is based on muscle contraction of the lower extremity. It is the general belief that contraction of the posterior musculature including gastrocnemius/- soleus muscles aid the return of fluid from the deep venous sinus in the lower extremity. It is the pumping mechanism of the muscles by changing the length and breadth of the structures that compress the venous sinus evacuating the pooled blood in those veins.

It was the belief that muscle contraction assisted venous return from the lower extremities that became the primary factor for initial research in use of electro stimulation of the lower extremities during surgical procedures to prevent venous stasis. The earliest use of galvanic stimulation for stasis prevention was by Doran. British Journal of Surgery, 511:486, 1964. Doran's method utilized calf muscle stimulation with galvanic current at 30 impulses per minute to promote fluid return of the lower extremities. This stimulation produced strong plantar-flexion of the foot throughout the operative procedure. A galvanic current was utilized to overcome the anesthetic agents used by anesthesiology which block the myoneuro junction of the muscles. Due to the operative theater, the unit was positioned on the left side of the patient, thereby stimulating only the left lower extremity.

There have been various researchers addressing the use of electrical stimulation to reproduce the physiologic activity of the calf muscles for the prevention of post operative thromboembolic complications. Original work by Nicolaides A. N., Kakkar V. V., and Field E. S. et al.: Optimal electrical stimulus for prevention of deep vein thrombosis, Br. Med. J. 3: 756–8, 1972, identified single electric pulses in the ranges of 12 to 15 pulses per minute to increase blood flow response from the lower extremities. More recently, Lindstrom B. et al.: Electrically induced short-lasting tetanus of the calf muscles for prevention of deep vein thrombosis, Br. J. Surg. 69:203–6, 1982, have shown pulse trained stimulation or groups of pulses to be three times more effective than the single pulse group. Early rationale by Lindstrom et al. also identified the posterior muscle pump mechanism to increase venous return. There is also documentation that the muscle stimulation through electrical current as well as sequential compression devices stimulate the release of fibrinolysin to inhibit the coagulation factors of the blood. In one study by Knight and Dawson published in *Lancet* in 1976, Vol. 1265, it was shown that intermittent pneumatic compression stimulated fibrinolytic activity to such an extent that the incidence of DVT in the legs was reduced.

Katz, Green, Sullivan and Yarkony, *Archives of Physical Medicine and Rehabilitation*, Vol. 68, July 1987, addressed functional electrical stimulation (FES) of muscles to decrease the incidence of post operative DVT in spinal cord injury patients. Their goal was to demonstrate the value of FES of calf muscles in increasing plasma fibrinolytic activity as well as promoting venous blood flow in the lower extremities. They found a significant increase in plasma fibrinolytic activity. Utilizing doppler ultrasound monitoring of venous flow, they also found a mild to moderate increase in venous return with FES. FES was found not to be as successful as manual compression in promoting emptying of the lower extremities. Stimulation parameters included pulse frequencies of 30 Hertz and pulse widths of 250 microseconds. Stimulation was applied once a minute for a duration of 4 seconds including a 2 second ramp-up. The intensity was sufficient to promote titanic contraction. Superficial electrodes were applied to the anterior and posterior compartments of the calf muscle and energized bilaterally. One electrode was placed over the muscle motor point, and one over the muscle tendon. Sixty minutes of alternating stimulation of the anterior/posterior compartment was achieved using the titanic contractions. Results of this study emphasized the need for FES to be incorporated into a large scale clinical trial in the prevention of DVT in acute spinal cord injury patients.

Research by Merli et al. described in the Archives of Physical Medicine and Rehabilitation, September 1968, evaluated the efficacy of low dose heparin alone or in combination with electrical stimulation in the prevention of DVT in $C_2$ to $T_{11}$ motor complete and incomplete preserved motor, non functional spinal cord patients. The tibialis anterior and gastrocnemius/soleus muscle groups were stimulated bilaterally producing cocontractions of anterior tibialis and gastrocnemius muscles. The stimulation utilized 50 microsecond pulses given at 10 Hertz with a 4 second on and 8 second off cycle for 23 hours daily over a 28 day period. The use of electrical stimulation plus low dose heparin significantly decreased the incidence of DVT compared to other treatments. However, the use of anticoagulants such as heparin can result in increased risk of hemorrhage. Also, there is an inherent inability to use anticoagulants in various neurosurgical and orthopedic situations. Finally, there is a necessity for ongoing blood tests to maintain safe therapeutic levels when using anticoagulants.

Another study by Nicolaides et al., published in *Surgery*, Vol. 94, pp. 21-5, July 1983, addressed intermittent sequential pneumatic compression of the legs and thromboembolism-deterrent (TED) stockings in the prevention of DVT. The study also included a group whereby electrical stimulation was applied to the calf. Galvanic stimulation with encircling type electrodes were utilized on the gastrosoleus muscle. The rate of stimulation was 12 pulses per minute and the amplitude was adjusted so a brisk plantar-flexion response of the foot was produced with only slight movement at the knee. The results of this study indicated that electrical stimulation was less effective than the regime of intermittent sequential compression and TED stockings.

The problem of DVT has therefore been addressed by Neuro-muscular electrical stimulation. It has not been used for two reasons.

First, it has been assumed that electrical muscle stimulation mimicked the pumping action of volitional muscle contraction, but any substantial increase in venous return had not been quantified and documented. Second, there was considerable stimulus-related pain associated with attempts to use neuro-muscular electrical stimulation (NMES) for DVT protection in the past. This pain was the result of posterior stimulation of the large gastrosoleu muscle and the use of standard pulsed NMES. To be accepted in clinical practice, the issue of pain reduction is important. Application techniques previously identified focused on cocontractions of anterior tibialis and gastrocnemius muscle or stimulation of the gastrocnemius muscle group. Finally, the type of stimulation and selected parameters did not appear to be appropriate to facilitate effective and sensory tolerable contractions of the appropriate muscle group.

SUMMARY OF THE INVENTION

The present invention addresses the use of neuromuscular electrical stimulation (NMES) of the lower extremity to promote venous return. The preferred embodiment is unique in that electrode placement addresses solely and exclusively the anterior to anterior lateral compartments of a patient's leg to produce dorsiflexion neutral inversion/eversion muscle stimulation as opposed to literature specific calf muscle stimulation for promoting venous return of deep veins in the patient's leg.

There was considerable stimulus related pain associated with attempts to use NMES for DVT protection in the past. Katz et al, Functional Electric Stimulation to Enhance Systemic Fibrinolytic Activity in Spinal Cord Injury Patients, *Archives of Physical Medicine and Rehabilitation*, Vol. 68(7), 423-26, July 1987. This was due to posterior electrode placement and use of standard pulsed NMES. The anterior nerves are more superficial than the posterior nerves making the stimulation less painful. To be accepted in clinical practice, this issue of pain reduction is important. In this regard, the anterior electrode placement coupled with the electrical stimulation parameters described in the present invention causes blood flow equal to or greater than that produced by the patient's own volitional contractions. The present invention also causes blood flow greater than that produced utilizing gastrocnemius muscle group or cocontraction of anterior tibialis and gastrocnemius muscle groups as done in previous studies and does so with less pain. The preferred embodiment also results in greater blood flow velocity than that produced by sequential compression devices.

In the preferred embodiment, electrodes are placed to activate a brisk contraction of the dorsiflexion muscle groups to maintain the foot in a neutral inversion/eversion dorsiflexed position. This dorsiflexion response is achieved with muscle contraction through a full available range of dorsiflexion. This contraction then leads to an active insufficiency of the dorsiflexion muscle group. In turn, the dorsiflexion component winds up the posterior compartment musculature and soft tissue structures to elicit an eventual passive insufficiency mechanism of those structures. This passive insufficiency response increases the compression and forces on the venous sinus to promote fluid return from the deep sinus regions of the posterior calf.

The preferred electrical stimulation is comprised of approximately 2500 Hertz carrier frequency current which is then pulse modulated at a rate of approximately 60 pulses per second. Although other carrier frequencies and pulse modulation rates also achieve the desired results, the above combination was found to render excellent results. Stimulation of the anterior compartment is performed periodically, preferably with a train of modulated pulses lasting for approximately 5 seconds followed by a rest period of 55 seconds. The preferred stimulation is started with about a 1 second ramp from minimum to maximum pulse value, and is concluded with approximately a 0.5 second ramp whereby the pulse train falls from its maximum value to zero. This burst stimulus causes a near optimal muscle pumping action for venous return and causes the patient less sensory pain than conventional square pulses.

Stimulation of the anterior and anterior lateral compartments produces a fused contraction that is balanced between the anterior tibialis, extensor hallucis longus, extensor digitorum longus, peroneus brevis, and the peroneus longus muscles. The passive stretching phenomena of the posterior musculature soft tissue group includes the tibialis posterior, flexor digitorum longus, flexor hallucis longus, tendon of the plantaris muscle, gastrocnemius and soleus, as well as the compartmental facia and the posterior tibial veins and perineal veins of this deep vascular sinus.

BRIEF DESCRIPTION OF THE DRAWINGS

FIG. 5 illustrates a typical blood flow curve as measured by doppler ultrasound venous imaging in response to a stimulation window with the characteristics of FIG. 1.

DETAILED DESCRIPTION OF THE INVENTION

Deep Vein Thrombosis (DVT) is a medical condition where a thrombus (blood clot) forms in a vein, typically in the lower extremity. A major contributing factor to the formation of a clot is stasis, or pooling of venous blood. The natural mechanism for assisting in the return of venous blood in an ambulatory, healthy individual is the process of walking where the contractions and extensions of the muscles in the lower extremity mechanically "pump" the venous blood through a series of valves in the venous system.

Patients who are immobile are at risk for DVT because they do not benefit from this intrinsic pumping action. It is however possible to cause a contraction of these muscles through electrical stimulation. From a practical perspective, it is important to provide adequate stimulation (amplitude and time) to cause the desired muscle group to contract in a manner that is comfortable to the patient. The preferred embodiment described hereinafter provides a sinusoidal stimulus with a 50% duty cycle for a nominal period of 3 to 10 seconds.

Figure 1:
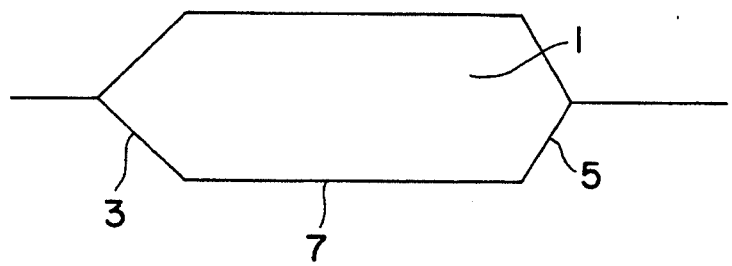
FIG. 1 illustrates a typical stimulation window showing the rise time, plateau (steady state) time and fall time for a 50% duty cycle sinusoidal electrical stimulation applied to a patient for causing the desired muscle group to contract in a manner that is comfortable to the patient.

Referring now to FIG. 1, there is illustrated a typical stimulus window 1 for the preferred embodiment. Each window is produced by a single train of pulse modulated signals having a carrier frequency about 2500 Hz. A 50% duty cycle sinusoid (1000 Hz–10,000 Hz) is gated by this window. The rise time 3 and fall time 5 cause a gradual stimulus onset and offset which are more comfortable than an instantaneous onset/offset. In addition, the gradual rise time creates a more efficient pumping action. A gradual rise time is essential in the preferred embodiment to limit a rapid contraction of the involved muscles which in effect caps off the venous return path.

A too rapid rise time effectively "caps" the venous return path thereby limiting the pumping effectiveness. The rise time shape is not limited to a linear rise. A cosine/plateau window would also be effective. In the preferred embodiment, empirically determined times which work well with a linear window are illustrated in FIG. 1. They include about a 1.0 second rise time, about a 0.5 second fall time and an on time of about 4.0 seconds, although an on time of between about 3 and 10 seconds is effective as hereinbefore stated.

Figure 2:
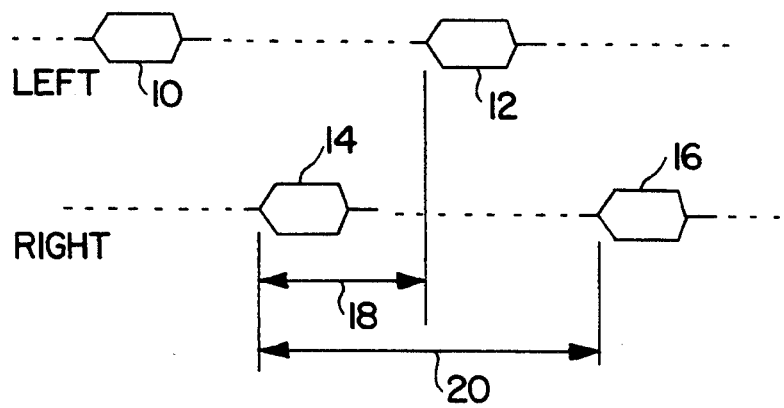
FIG. 2 illustrates a preferred stimulation technique applied to both legs of a patient bilaterally. It is also possible to deliver the stimulus synchronously.

This stimulation technique of the preferred embodiment is applied to both legs. Typically, the stimulus 10, 12, 14, 16 is delivered alternately to both legs for reasons of comfort, as illustrated in FIG. 2 of the preferred embodiment. In an alternative embodiment, it is also possible to deliver the stimulus synchronously. In the preferred embodiment, each leg is typically stimulated once per minute 20 thereby providing one pumping action each minute 18, 20 for each leg. This is consistent with the stimulus periodicity used with sequential compression devices known in the prior art.

Figure 3:
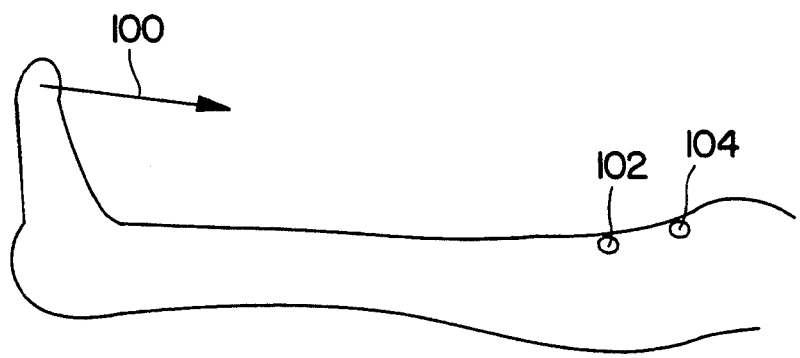
FIG. 3 illustrates a preferred stimulation location for stimulating the common peroneal nerve transcutaneously on the anterior portion of a patient's knee thereby causing dorsiflexion contraction within the patient's leg(s).

Moving now to FIG. 3 of the preferred embodiment, the stimulus location 102, 104 with a corresponding contraction 100 which was most effective in causing an increase in blood flow velocity is illustrated. Simulating the common peroneal nerve transcutaneously on the anterior portion of the knee causes a dorsiflexion contraction. A typical blood flow curve to this type of stimulation is illustrated in FIG. 5.

FIG. 5 illustrates a typical blood flow curve as measured via doppler ultrasound venous imaging in response to a stimulation window with the characteristics of the preferred embodiment shown in FIG. 1. Desirable increases in blood flow velocity occur both during the onset of stimulation 200 and during the offset 202 of stimulation. The blood flow elicited by the stimulated peroneal nerve thereby causing dorsi-flexion muscle contraction 100 was found to be nominally 2.5 times higher than the patient resting flow and 2 times that obtainable with sequential compression devices.

Figure 4:
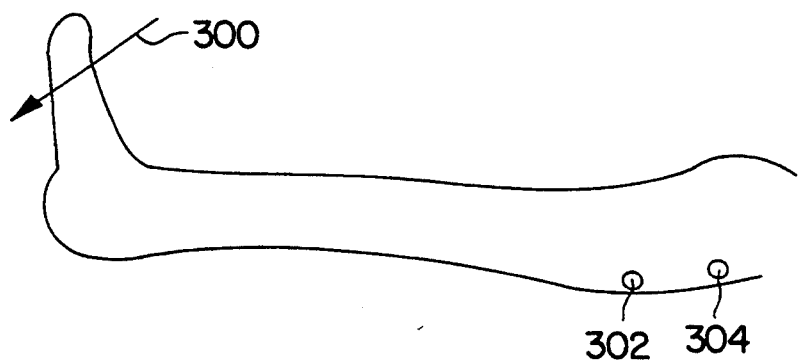
FIG. 4 illustrates stimulation of the tibial nerve on the posterior portion of a patient's knee as known in the prior art.

Voluntary planter-flexion 300 has been used post-surgically with push-boards placed at the foot of the bed to enhance venous circulation post-surgically. Earlier work, illustrated in FIG. 4, and described in the prior art, identified stimulation of the tibial nerve on the posterior knee 302, 304 for the same reason. The prior art literature describes limited efficacy with this protocol. Stimulation of the tibial nerve did not yield significant increases in venous blood velocity as routinely caused by peroneal nerve stimulation as illustrated in FIG. 5 of the preferred embodiment. Peroneal nerve stimulation for the preferred embodiment illustrated in FIG. 3, causes a passive stretching of the gastrocnemius and soleus muscles (major posterior calf muscles) instead of a contraction for the pumping action. Lacking this insight has virtually eliminated the use of Neuromuscular Stimulation for the treatment of Deep Vein Thrombosis.

While the invention has been described above in connection with the particular embodiments and examples, one skilled in the art will appreciate that the invention is not necessarily so limited. It will thus be understood that numerous other embodiments, examples, uses, modifications of, and departures from the teachings disclosed may be made, without departing from the scope of the present invention as claimed herein.

For example, it is not necessary that the invention be practiced utilizing a 2500 Hz carrier frequency as described in the preferred embodiment. Other carrier frequencies may also be employed. The preferred pulse modulation rate may also be altered from 60 per minute and still render satisfactory results. It is therefore apparent that many combinations of electrical stimulus parameters will achieve successful results so long as the electrodes are placed as hereinbefore described.

What is claimed is:

1. A method of treatment and prevention of deep vein thrombosis in a lower extremity of an immobilized patient, the method comprising:

placing a plurality of electrodes on an anterior portion of at least one knee of the immobilized patient, proximal a common peroneal nerve of said patient; and applying an electrical current to said electrodes while the patient remains immobilized thereby stimulating the common peroneal nerve transcutaneously, such that dorsiflexion muscle stimulation is produced, whereby blood flow in the deep leg veins of said patient is increased with minimal pain imparted to said patient.

2. The method of claim 1 wherein said electrical current includes a train of modulated pulses for reducing pain associated with the application of said electrical current.

3. The method of claim 2 wherein said train is periodically applied.

4. The method of claim 3 wherein said period has an on time about 4 seconds and an off time about 55 seconds.

5. The method of claim 4 wherein said train has a rise time about 1 second.

6. The method of claim 5 wherein said train has a fall time about 0.5 seconds.

7. The method of claim 6 wherein said train has a carrier frequency current about 2500 Hertz.

8. The method of claim 7 wherein said carrier frequency current is pulse modulated.

9. The method of claim 8 wherein said pulse modulation is performed at a rate of about 60 pulses per second.

10. A method of treatment and prevention of deep vein thrombosis in a lower extremity of an immobilized patient, the method comprising:
 (a) placing a first plurality of electrodes on an anterior portion of a first knee of the immobilized patient, said electrodes placed proximal a common peroneal nerve of said patient and a second plurality of electrodes on an anterior portion of a second knee of the immobilized patient, said electrodes placed proximal a common peroneal nerve of said patient;
 (b) applying an electrical current for a predetermined period of time to said first electrodes on said first knee while the patient remains immobilized thereby stimulating the common peroneal nerve on said first knee transcutaneously, such that dorsiflexion muscle stimulation is produced;
 (c) applying an electrical current for a predetermined period of time to said second electrodes on said second knee while the patient remains immobilized thereby stimulating the common peroneal nerve on said second knee transcutaneously, such that dorsiflexion muscle stimulation is produced; and
 (d) repeating steps (b) and (c).

11. The method of claim 10 wherein the application of electrical current in step (b) is synchronized with the application of electrical current in step (c).

12. The method of claim 11 wherein the electrical current is applied sequentially to the first and second electrodes.

* * * * *